United States Patent
Huefner et al.

(10) Patent No.: US 9,216,231 B2
(45) Date of Patent: Dec. 22, 2015

(54) STERILIZATION APPARATUS AND METHOD FOR CONTROLLING OF A STERILIZATION APPARATUS

(75) Inventors: Gerhard Huefner, Frankfurt am Main (DE); Matthias Henrich, Frankfurt am Main (DE); Michael Willems, Frankfurt am Main (DE)

(73) Assignee: Sanofi-Aventis Deutschland GmbH, Franfurt am Main (DE)

( * ) Notice: Subject to any disclaimer, the term of this patent is extended or adjusted under 35 U.S.C. 154(b) by 561 days.

(21) Appl. No.: 13/501,043

(22) PCT Filed: Oct. 8, 2010

(86) PCT No.: PCT/EP2010/065098
§ 371 (c)(1),
(2), (4) Date: Dec. 3, 2012

(87) PCT Pub. No.: WO2011/042541
PCT Pub. Date: Apr. 14, 2011

(65) Prior Publication Data
US 2013/0071288 A1      Mar. 21, 2013

(30) Foreign Application Priority Data
Oct. 9, 2009   (EP) .................................... 09172650

(51) Int. Cl.
*A61L 2/06*   (2006.01)
*A61L 2/24*   (2006.01)
(Continued)

(52) U.S. Cl.
CPC ... *A61L 2/06* (2013.01); *A61L 2/24* (2013.01); *B65B 55/027* (2013.01); *B65B 55/10* (2013.01)

(58) Field of Classification Search
CPC .......................................................... A61L 2/06
USPC ............................................................ 422/1
See application file for complete search history.

(56) References Cited

U.S. PATENT DOCUMENTS 3,683,692  A   8/1972 Lafitte
2007/0237670 A1   10/2007 Snyder et al.

FOREIGN PATENT DOCUMENTS

DE   2100769           9/1971
DE   4131258 A1        5/1992
DE   19709067 A1       9/1998
(Continued)

OTHER PUBLICATIONS

English machine translation of DE 4131258. Siedler et al. May 7, 1992.*

(Continued)

*Primary Examiner* — Sean E Conley
*Assistant Examiner* — Donald Spamer
(74) *Attorney, Agent, or Firm* — McDonnell Boehnen Hulbert & Berghoff LLP

(57) ABSTRACT

The invention relates to a sterilization apparatus (10) and to a method for the sterilization of an object (7) by a gaseous or liquid fluid comprising: a sterilization chamber (8) in which the object (7) is positioned, at least an acceleration device (2) for accelerating the fluid to a predetermined flow-speed, at least a filter device (3) for separating particles from the fluid, characterized in that the sterilization apparatus further comprises at least an orifice device (4) providing a plurality of openings, and a control apparatus for determining the flow-speed of the fluid on the basis of a pressure difference ($\Delta p$).

17 Claims, 1 Drawing Sheet

(51) Int. Cl.
*B65B 55/02* (2006.01)
*B65B 55/10* (2006.01)

(56) References Cited

FOREIGN PATENT DOCUMENTS

EP 0570946 A1 11/1993
EP 0312022 A2 4/1998

OTHER PUBLICATIONS

"Ideal Gas Law". wikipedia.org. Archived version from Oct. 2, 2009.*
"Orifice, Nozzle, and Venturi Flow Rate Meters". Engineering Toolbox. Retrieved from Internet Archive Wayback Machine capture from Sep. 27, 2009.*
Form PCT/IB/326, Notification Concerning Transmittal of Copy of International Preliminary Report on Patentability.

* cited by examiner

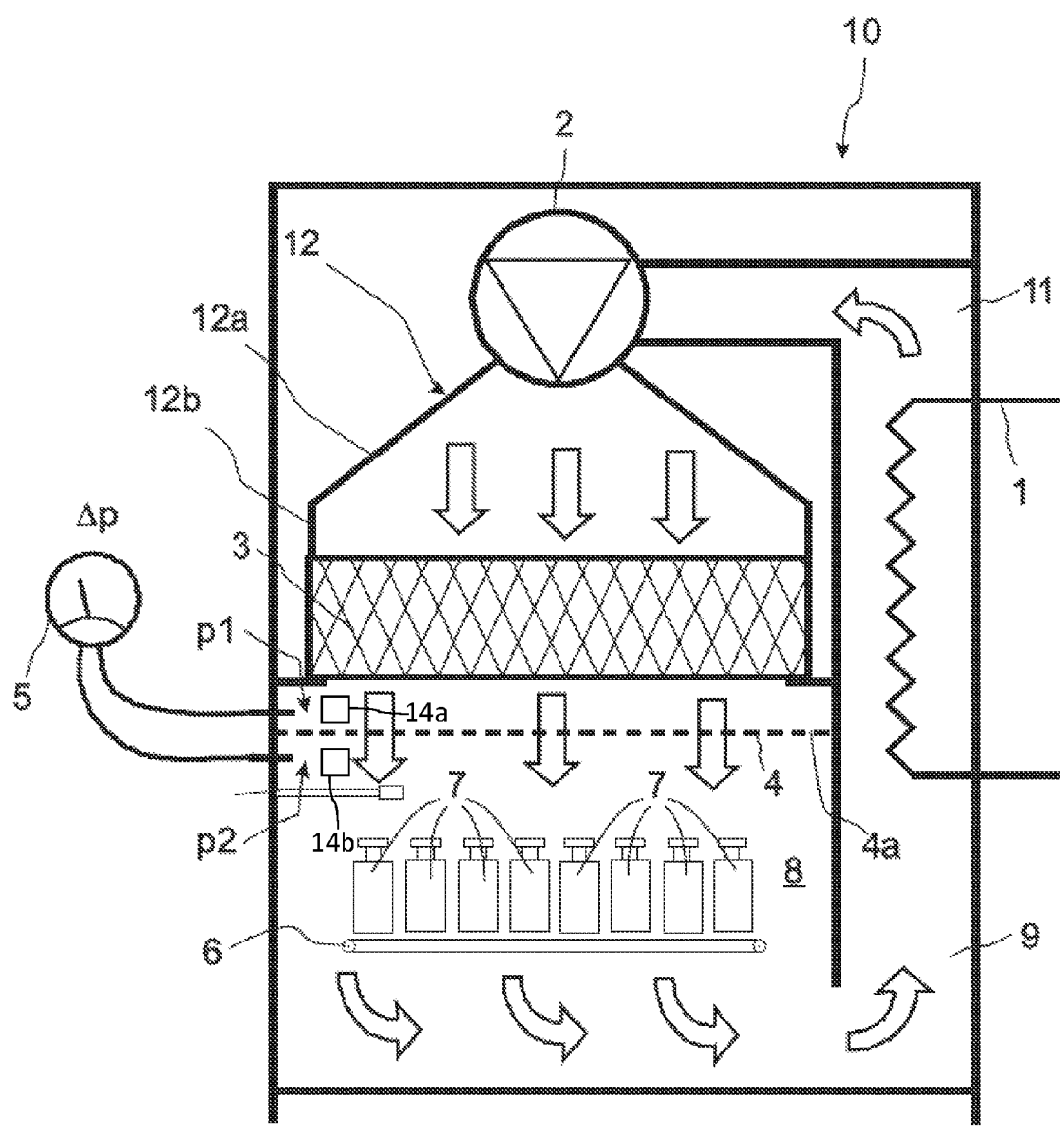

STERILIZATION APPARATUS AND METHOD FOR CONTROLLING OF A STERILIZATION APPARATUS

CROSS REFERENCE TO RELATED APPLICATIONS

The present application is a 35 U.S.C. 371 National Application of PCT/EP2010/065098 filed Oct. 8, 2010, which claims priority to European Patent Application No. 09172650.5, filed Oct. 9, 2009, the entire contents of which are incorporated entirely herein by reference.

The invention relates to a sterilization apparatus for controlling the sterilization of at least one object by a gaseous or liquid fluid wherein the object is positioned in a sterilization chamber of a sterilization apparatus, and to a method for controlling of the sterilization of an object by a heated fluid wherein the object is positioned in a sterilization chamber of a sterilization apparatus.

In common sterilization apparatuses mainly two different sterilization technologies can be distinguished in which objects like for instance medical syringes or ampoules get rid of a contamination with bacteria or viruses. First there is the ray sterilization, in which the object to be sterilised is irradiated with for instance y-rays in order to obtain a fully sterilised object. This method is applied preferably when the objects to be sterilised are not resistant to high temperatures. A second method is the heat-sterilization in which a fluid is heated up to a sufficiently high temperature, and then blown into a chamber in which the object to be sterilised is positioned. In a slightly modified process the fluid may be gaseous, preferably air, which is called the dry-heat sterilization when there is substantially no humidity left in the sterilization fluid.

In the latter process, the quality of the sterilization depends on the time duration the object is exposed to the fluid and on the quantity of fluid mass flow which is getting in contact with the object to be sterilised. Thereby not only the fluid-temperature but also the flow-speed of the fluid is a crucial factor with a high impact on the sterilization result. Accordingly, in a sterilization apparatus it is important to determine the flow-speed of the fluid with a sufficiently high accuracy.

In the prior art in general there are shown two different principals of measuring the speed in a flowing fluid. For instance the DE 2100769 shows an apparatus for measuring the flow-speed of a gaseous fluid by using a temperature element which changes its resistance depending on the environmental temperature, the so called hot wire anemometer. Thereby the temperature element is heated up to a predetermined temperature and when a fluid flows around the sensor, the sensor itself is cooled down. The cooling effect leads to a variation in the resistance value of the sensor from which the flow-speed can be derived. This method however has drawbacks regarding its accuracy, when the sensor element is subjected to fluid with high temperature. In a high temperature range the density of gaseous fluids is rather low so that an exact measurement can not be carried out.

Document US 2007/0237670 A1 discloses a dry heat sterilization system comprising semi-pierced duct walls inside a chamber. Furthermore, safety airflow switches are provided that can shut down a heater if they sense that there is no air flowing over the heater. The safety airflow switches are pressure differential switches that measure airflow of an air intake and an air outlet being arranged outside the sterilization chamber.

Further, there are known sterilization apparatuses which use vane anemometers for measuring the flow-speed of the fluid, the so called impeller anemometer. Such anemometers are disposed in the flow of the fluid which is used to sterilise an object in a later stage. However, such mechanical anemometers can not withstand or resist the high temperatures used for the sterilization for a long term and therefore have to be replaced in order to avoid breakdown of the entire sterilization apparatus.

Furthermore with the above mentioned anemometers only punctual measurement of the flow-speed can be carried out. Usually, the sterilization apparatuses have a relatively large cross section area for the fluid flow. Since the flow is measured only in a rather small area there remains the danger that even though a correct value in the measurement area is determined, in the rest of the cross section an inappropriate flow-speed may remain undetected.

A further problem has to be seen in the fact, that known anemometers are calibrated for a fluid having a density of 1.2 kg/m$^3$. However, during a sterilization process the fluid can reach temperatures of about 300° C. where the fluid's density drops to 0.6 kg/m$^3$ leading to ineligible deviation in the measurements accuracy.

In the light of the above mentioned difficulties, the present invention addresses the object to provide a control apparatus and a method for controlling the sterilization of objects wherein the measurement of the flow-speed can be carried out with improved accuracy.

This object is solved by an apparatus and a method according to the independent claims. Further embodiments and examples of the invention are subject matter of the dependent claims which are referred back thereto.

According to an aspect of the invention a sterilization apparatus for the sterilization of at least one object by a gaseous or liquid fluid comprises a sterilization chamber in which the object is positioned, at least an acceleration device for accelerating the fluid to a predetermined flow-speed and at least a filter device for separating particles from the fluid.

The sterilization apparatus further comprises at least one orifice device having a plurality of openings and being preferably arranged or disposed in the flow-path of the fluid inside the sterilization chamber. Furthermore, the sterilization apparatus comprises a control apparatus for determining the flow-speed of the fluid on the basis of a pressure difference across the orifice device.

In a further aspect, the apparatus is characterized in that the pressure difference is derived and determined from a first and second pressure, wherein the first pressure is measured in the fluid-flow upstream of the orifice device and wherein the second pressure is measured in the fluid-flow downstream of the orifice device.

Such an arrangement provides the advantage, that the first pressure on the upstream side of the orifice device is nearly constant over the entire cross section of the orifice device. The same applies to the second pressure measured on the downstream side of the orifice device. Accordingly, it is possible to determine with a single, punctual measurement the first and second pressures over the entire cross section of the orifice device and hence across the entire cross section of the fluid-flow. By making use of the orifice device and the arrangement of respective pressure sensors arranged upstream and downstream the orifice device, the flux of the fluid directed to the at least one object can be determined with high accuracy.

According to another embodiment, the first and a second pressure sensors are disposed upstream and downstream of the orifice device, respectively, wherein the first pressure sensor is disposed downstream of the filter device and wherein the second pressure sensor is disposed upstream of the at least one object to be sterilized.

At least the second pressure sensor, preferably both pressure sensors are disposed inside the sterilization chamber.

First and/or second pressure sensors can be arranged in the center but also near the lateral side edge of the orifice device.

According to another embodiment, the apparatus comprises at least a heating device for heating the fluid to a predetermined sterilization-temperature. The apparatus further comprises a guiding channel to guide the fluid from the heating device to the acceleration device. Downstream of the acceleration device, the filter and the orifice device are disposed in sequential manner. Hence, the filter device is arranged downstream of the acceleration device and the orifice device is arranged downstream of the filter device but upstream of the at least one object. Accordingly, the heated and accelerated fluid is guided through the filter device and thereafter through the orifice device to the at least one object disposed in the sterilization chamber.

Additionally, the apparatus may further comprise at least a fluid-temperature determining device, for determining a temperature of the fluid. The fluid-temperature determining device may comprise a thermometer or temperature sensor disposed in the fluid-flow, preferably inside the sterilization chamber and/or outside the sterilization chamber for determining or measuring the temperature of the heated fluid and/or the temperature of ambient air.

According to another embodiment, the apparatus further comprises a comparison device for comparing a measured value of the flow-speed with a predetermined minimum value of the flow-speed and/or with a predetermined maximum value of the flow-speed, wherein the comparison device is adapted to generate a flow-speed failure-signal when the measured value exceeds the predetermined maximum value of the flow-speed or when the measured value falls below the predetermined minimum value of the flow-speed. Furthermore, the comparison device is adapted to compare a measured value of the fluid-temperature with a predetermined minimum value of the fluid-temperature and/or with a predetermined maximum value of the fluid-temperature, wherein the comparison device is further adapted to generate a fluid-temperature failure-signal when the measured value of the fluid-temperature exceeds the predetermined maximum value of the fluid-temperature or when the measured value falls below the predetermined minimum value of the fluid-temperature.

Furthermore, and according to another embodiment, the apparatus is further characterised in that, the predetermined minimum value of the fluid-flow-speed is 0.5 m/s and/or the predetermined maximum value of the fluid-flow-speed is 1.2 m/s, and/or the predetermined minimum value of the fluid-temperature is around 200° C. and/or the predetermined maximum value of the fluid-temperature is around 500° C.

Moreover, the apparatus may further comprise a calculation device for calculating the flow-speed value of the sterilization fluid on the basis of the determined pressure difference and on the basis of a measured temperature of the fluid.

According to another embodiment, the apparatus is further characterized in that the calculation device is adapted to determine whether the fluid is apt for a sufficient sterilization of the object on the basis of the determined flow-speed of the fluid, a predetermined time period the at least one object is exposed to the fluid in the sterilization chamber, and/or on the basis of the temperature of the fluid, and wherein the calculation device and/or the control apparatus are adapted to generate a first signal for increasing and/or decreasing the flow-speed and/or to generate a second signal for increasing and/or decreasing the fluid-temperature in response to determine that the fluid is not apt to sufficiently sterilize the at least one object.

In particular, the control apparatus is adapted to generate and/or to transmit a first signal to the accelerating device in response to a determination, that the conditions of the fluid are not suitable to sufficiently sterilize the at least one product. Upon receipt of the first signal, the control apparatus is adapted to increase and/or to decrease to flow-speed by manipulating the acceleration device accordingly. In a similar way, the control apparatus is adapted to generate and/or to transmit a second signal to the heating device for increasing and/or decreasing the fluid-temperature, respectively.

The apparatus may further comprise a positioning device for positioning and/or moving the at least one object to be sterilized into the fluid flow. Preferably, by way of the positioning device, the at least one or a plurality of objects can be positioned and moved into an area, in which they are exposed to the fluid flow.

According to another embodiment, the positioning device comprises a temperature resistive belt-conveyor suitable for providing a continuous or step-wise transfer of a plurality of objects to be sterilized by way of the fluid flow.

In another preferred embodiment, the fluid is confined in a closed circuit wherein after sterilization of the at least one object the fluid is guided through a feed back channel and is fed back to the heating device.

In still another embodiment the apparatus further comprises a stopping device, which is adapted to process a flow-speed failure signal and/or a fluid-temperature failure signal for stopping and/or throttling the acceleration device and/or the heating device. In this way, overheating of the apparatus can be substantially prevented.

In a further aspect the invention relates to a method for controlling of the sterilization of at least one object by a heated gaseous or liquid fluid wherein the at least one object is positioned in a sterilization chamber of a sterilization apparatus, inside which the object is sterilized by exposure to the fluid, wherein the method comprises the steps of: accelerating the fluid to a predetermined flow-speed by means of an acceleration device, separating particles from the fluid by means of a filter device and guiding the fluid through a plurality of openings in an orifice device arranged in the flow-path of the fluid and determining the flow-speed of the fluid on the basis of a pressure difference across the orifice device comprising a plurality of openings.

According to a further embodiment, the pressure difference is determined by comparing a first pressure measured upstream of the orifice device, and a second pressure measured downstream of the orifice device. By comparing first and second pressures a pressure difference can be obtained by e.g. subtracting the measured first and second pressures, wherein the pressure difference in the direction of flow across the orifice device is a direct indication for the flow speed to be determined.

Additionally, the method may be characterized by the step of heating the fluid up to a predetermined sterilization-temperature by means of a heating device.

Moreover, the controlling method may comprise determining a temperature of the fluid.

According to another preferred embodiment, the flow speed $\omega$ is calculated as $$\omega = \Phi \cdot \sqrt{\frac{2 \cdot \Delta p \cdot R_i \cdot (\tau + 273)}{p_{air}}},$$

with $R_i$ being the gas constant of air, $\Delta p$ being the determined pressure difference, $\tau$ being the measured fluid-temperature, $p_{air}$ being the ambient air pressure, and $\phi$ being a characteristic value of the orifice device.

In addition to this the method may comprise comparing a measured value of the flow-speed with a predetermined minimum value of the flow-speed and with a predetermined maximum value of the flow-speed, and generating a flow-speed failure-signal when the measured value exceeds the predetermined maximum value of the flow-speed or when the measured value drops below the predetermined minimum value of the flow-speed and/or comparing a measured value of the fluid-temperature with a predetermined minimum value of the fluid-temperature and with a predetermined maximum value of the fluid-temperature, and generating a fluid-temperature failure-signal when the measured value of the fluid-temperature exceeds the predetermined maximum value of the fluid-temperature or when the measured value drops below the predetermined minimum value of the fluid-temperature.

Furthermore, the method may comprise calculating the flow-speed value of the fluid on the basis of the determined pressure difference and the measured temperature of the fluid.

Additionally, the method may comprise receiving an input signal specifying a predetermined time period the object remains positioned in the sterilization chamber, by a calculation device, determining on the basis of the input signal and the calculated flow-speed whether the condition of the fluid is apt for a sufficient sterilization of the object during the predetermined time period, by the calculation device. If it is determined, that the condition of the fluid is not apt for a sufficient sterilization, a first signal will be generated and transmitted to the accelerating device for increasing and/or decreasing the flow-speed and/or a second signal will be generated and transmitted to the heating device for increasing or decreasing the fluid-temperature, respectively.

Moreover, the method may be characterized by feeding back of the fluid to the heating device after sterilization of the object by guiding it through a feed back channel. In addition to this, a flow-speed failure-signal and/or a fluid-temperature failure-signal may be received from the comparison device and may be further processed by a stopping device for stopping and/or throttling the acceleration device when the stopping device receives at least one of the failure-signals.

Furthermore, the method may conduct dry heat sterilization for sterilizing the at least one object.

It will be apparent to those skilled in the art, that various modifications and variations can be made to the present invention without departing from its spirit and scope. Further, it is to be noted, that any reference signs used in the appended claims are not to be construed as limiting the scope of the present invention.

The invention will be understood in greater detail from the following description of the preferred embodiments thereof, which are given only by way of example and with reference to the accompanying drawing, in which FIG. 1 is a schematic side view of a sterilization apparatus.

In FIG. 1 the schematic configuration of a sterilization apparatus 10 according to the invention provided with a control apparatus is illustrated. The sterilization apparatus 10 uses a fluid for the sterilization of objects 7, wherein the fluid can be in a gaseous or in a liquid state. The expression object is used as a synonym for medical devices, like especially ampoules, cartouches, vials, heat resistant syringes, needles, multi dosage containers and/or carpoules. The sterilization apparatus relates therefore to a dry-heat-sterilization type apparatus, wherein a fluid is used for transferring heat to the objects.

In following the constitution of the sterilization apparatus is described by following up the path of the fluid through the sterilization apparatus 10. In a heating device 1 the fluid is heated up until it reaches a fluid-temperature which is suitable or apt for a sufficient sterilization of the object 7. The heating device 1 can comprise an electrical heater or a combustion heater for instance. For a sufficient sterilization the fluid temperature has to lie within an interval between 200° C. and 500° C. preferably between 260° C. and 320° C.

The sterilization apparatus 10 furthermore comprises an accelerating device 2 for accelerating the fluid, whereby the fluid is sucked from the heating device 1 through a guiding channel 11 to the accelerating device 2. Preferably, the acceleration device 2 comprises a fan, a blower or a turbine. From the accelerating device 2 the fluid is transferred into a filter chamber 12 comprising a cone-formed inlet 12a and a filter seat 12b. When passing through the cone-formed inlet 12a the fluid-flow laterally spreads from a small cross section in the acceleration device 2 to a larger cross section in the cone-formed inlet 12a such that a nearly constant laminar and homogeneous flow is created. In the filter seat 12b a filter 3 is positioned for filtering particles from the fluid which may be present in the fluid as impurities or pollution and which may therefore deteriorate the sterilization of the object 7.

After exiting the filter 3 the fluid passes through an orifice device 4, which is situated on a downstream side of the filter 3. The orifice device 4 is provided with a plurality of openings 4a oriented in the fluid flow direction such that the fluid can pass there through. The orifice device typically comprising a planar structure is oriented in a direction perpendicular to the flow direction of the fluid. Hence, the surface normal of the planar structure is aligned substantially parallel to the direction of flow. This orifice device 4 may be built as a perforated metal plate, made of a thermo resistant stainless steel and therefore constricts the cross section of the fluid-flow. It therefore induces a pressure drop in the fluid from a first pressure p1, which is present upstream of the orifice device 4, to a second pressure p2 situated on a downstream side of the orifice device 4. By measurement of these two pressures p1 and p2 by means of at least two separate pressure sensors 14a, 14b, a pressure difference $\Delta p$ can be determined by a calculation device 5. This pressure difference $\Delta p$ is proportional to the fluid flow-speed in the fluid flow so that a flow-speed of the fluid can be easily calculated. First and second pressures are measured by means of respective pressure sensors 14a, 14b arranged in the fluid-flow path.

Downstream of the orifice device 4 a sterilization chamber 8 is provided in the sterilization apparatus 10 for receiving the objects 7 to be sterilized. In the sterilization chamber 8 at least one single object 7 is exposed or a plurality of objects 7 are exposed to the heated fluid, in order to become sterilized. Thereby the object 7 is placed on a positioning device 6, which can be embodied as table or a holder. In an alternative embodiment the objects 7 are placed one after another on a conveyor belt which embodies the positioning device 6.

Alternatively, the orifice device 4 may not be provided on an upstream side of the sterilization chamber 8, but may be integrated in the sterilization chamber 8. In such an embodiment the sterilization chamber 8 is adjacent to the filter chamber 12. In other words, when the fluid exits the filter chamber 12, it immediately enters the sterilization chamber 8.

When flowing through the sterilization chamber 8 the fluid gets in contact with the object 7 and due to the high fluid-temperature the objects are sterilised. Then the fluid exits the sterilization chamber 8 and is guided through a feed-back channel 9 to the heating device 1. In the embodiment shown in FIG. 1 the fluid used for the sterilization is kept and confined in a closed circuit wherein the flow is perpetuated by the accelerating device 2.

In an alternative embodiment, the sterilization apparatus can be formed as an open system, wherein the fluid is sucked into the heating device 2 from the environment and after passing the same path as described above relating to the closed system, it is blown into the environment again.

In the following the sterilization process is described in more detail. The conveyor belt 6 transfers the objects 7 through the sterilization chamber 8 with a predetermined velocity, which means that the objects remain in the sterilization chamber 8 only for a predetermined period of time. It must be assured that during this time period the object 7 is sufficiently sterilised by the fluid. Therefore, the flow-speed of the fluid should provide a value in the interval between 0.5 m/s and 1.2 m/s preferably around 0.8 m/s. In this speed-range advantageously the signal of the determining device 5 is nearly constant and comprises only very small variations or fluctuations.

Accordingly, for the sterilization process, the following factors: the period of time the object is exposed to the heated fluid, the fluid temperature and the speed of the fluid have an important impact on the sterilization result. Moreover, the period of time, the object is exposed to the heated fluid, is a function of the conveyor belt velocity of circulation. Departing from the time period which is a rather fixed value, the temperature and the velocity of the fluid must be controlled in order to provide sufficient sterilization results.

As mentioned above, the flow-speed is calculated on the basis of a pressure difference measured by pressure sensors 14a, 14b and determined by a determining or calculation device 5. The fluid-temperature is also measured by a respective sensor provided in the flow stream. The actual flow-speed is then calculated by a calculation device 5 using the following equation:

$$\omega = \Phi \cdot \sqrt{\frac{2 \cdot \Delta p \cdot R_i \cdot (\tau + 273)}{p_{air}}}.$$

Wherein, the placeholders represent:
$R_i$: the gas constant of air,
$\Delta p$: the determined pressure difference,
$\tau$: the measured fluid-temperature,
$p_{air}$: the ambient air pressure, and
$\phi$: a characteristic value of the orifice device.

The characteristic value $\phi$ is dependent on the geometry and shape of the sterilization apparatus, as well as the size and form of the openings provided in the orifice device 4. This calculation method further takes into consideration the deviation of the fluid temperature, so that the sterilization apparatus can be operated at a variety of different fluid-temperatures. In other words, it is possible to control the flow-speed and/or the temperature even in case of a variation of the fluid-temperature and/or to modify the temperature and/or the flow-speed in case of a variation of the flow-speed.

In addition, with a configuration according to the invention it becomes possible to change the period of time the objects 7 are exposed to the heated fluid and/or remain in the sterilization chamber 8, for instance by modifying the conveyor belt velocity. This however requires a change in the fluid temperature. For instance when the conveyor belt velocity is increased the fluid-temperature should be increased for maintain the required sterilization quality. On the other hand, when said time period is prolonged, for instance by reducing the conveyor belt velocity, for economical reasons the fluid-temperature can be reduced while the same sterilization quality can be attained.

The invention provides therefore the advantage that with taking into consideration the fluid-temperature the flow-speed can be calculated with a high accuracy.

For assuring that the sterilization apparatus is operating with a correctly and/or predetermined conditioned fluid, a comparison device is provided for comparing the measured value of the flow-speed with a predetermined minimum value of the flow-speed and/or with a predetermined maximum value of the flow-speed. In other words the comparison device compares whether the flow-speed is e.g. within the given interval between 0.5 m/s and 1.2 m/s or not. If the measured value exceeds the predetermined maximum value of the flow-speed and/or if the measured value falls below the predetermined minimum value of the flow-speed, the comparison device generates a flow-speed failure-signal.

Alternatively or in addition to this, the comparison device compares the measured value of the fluid-temperature with a predetermined minimum value of the fluid-temperature and/or with a predetermined maximum value of the fluid-temperature, i.e. the comparison device checks if the fluid-temperature lies within the predetermined interval mentioned above, namely between 200° C. and 500° C. If the measured value of the fluid-temperature exceeds the predetermined maximum value of the fluid-temperature and/or if the measured value drops below the predetermined minimum value of the fluid-temperature, the comparison device will generate a fluid-temperature failure-signal.

In an embodiment of the invention these failure-signals are displayed to a user of the sterilization apparatus for instance on a display, by using a warning lamp and/or by generating a warning sound. Thereby the temperature failure signal and the flow-speed failure signal are displayed separately or simultaneously, depending upon which failure occurs.

In a further preferred embodiment the failure signals are generated and displayed by the comparison device and then received by a stopping device, which is apt for receiving and/or processing a flow-speed failure-signal and/or a fluid-temperature failure-signal from the comparison device. Based on the received signal the stopping device generates a signal for stopping and/or throttling the acceleration device 2 and/or the heating device 1. Accordingly, the control apparatus provides an emergency shutdown function in the case when at least one of the parameters leaves its admissible operating range.

In addition to this the calculation device receives an input signal including data specifying a predetermined time duration during which the object 7 is positioned in the sterilization chamber 8. This time period can be determined, even through input by a user via an input terminal or may be a fixed parameter. The calculation device determines on the basis of the given input time period and the calculated flow-speed whether the condition of the fluid is apt for a sufficient sterilization of the object 7 during the predetermined time period. In other words, the calculation device will autonomously decide if the real mass flow with the real temperature is apt for sterilizing the object 7, such that a desired sterilization result can be achieved. If the calculation device determines that the condition of the fluid is not apt for a sufficient sterilization, the control apparatus generates a first signal which is transmitted to the accelerating device 2 for increasing and/or decreasing the flow-speed such that the mass flow of the sterilization fluid becomes sufficient for attaining the required sterilization result.

Alternatively or additionally, the control apparatus generates a second signal which is transmitted to the heating device 1 for increasing or decreasing the fluid-temperature. So, the control apparatus is able to automatically correct a deviation in the fluid temperature by for instance increasing or reducing the heating power of the heating device 1. A deviation in the flow-speed can be corrected by the control apparatus by increasing or decreasing e.g. a fan speed of the accelerating device 2. The wording condition in this context has to be understood as a corresponding pair of fluid-temperature and flow-speed which have to fit together such that a correct sterilization is carried out.

The invention claimed is:

1. Sterilization apparatus for the sterilization of an object by a gaseous or liquid fluid comprising:
    a sterilization chamber in which the object is positioned,
    a filter chamber comprising a cone-formed inlet and a filter seat,
    at least an acceleration device for accelerating the fluid to a predetermined flow-speed, wherein the acceleration device is positioned on the cone-formed inlet,
    at least a filter device for separating particles from the fluid, wherein the filter device is positioned in the filter seat,
    at least an orifice device having a plurality of openings being arranged in a flow-path of the fluid, and
    first and second pressure sensors disposed upstream and downstream of the orifice device, respectively, wherein the first pressure sensor is disposed downstream of the filter device and wherein the second pressure sensor is disposed upstream of the at least one object to be sterilized.

2. Apparatus according to claim 1, further comprising a heating device for heating the fluid to a predetermined sterilization-temperature, and comprising a guiding channel to guide the fluid from the heating device to the acceleration device, wherein the filter device is arranged downstream of the acceleration device and wherein the orifice device is arranged downstream of the filter device but upstream of the objects positioned in the sterilization chamber.

3. Apparatus according to claim 1, further comprising at least a fluid-temperature determining device, for determining a temperature of the fluid.

4. Apparatus according to claim 1, further comprising a positioning device for positioning and/or moving the at least one object to be sterilized into the fluid flow.

5. Apparatus according to claim 4, characterized in that the positioning device is a temperature resistive belt-conveyor apt for step-wise or continuously moving a plurality of objects through the fluid flow.

6. Apparatus according to claim 1, further comprising a closed circuit for the fluid, wherein after sterilization of the object the fluid is guided through a feedback channel and fed back to the heating device.

7. The sterilization apparatus of claim 1 wherein the orifice device comprises a planar structure and is oriented in a direction perpendicular to the flow direction of the fluid.

8. The sterilization apparatus of claim 1 wherein the orifice device is built as a perforated metal plate comprising a thermo resistant stainless steel.

9. Method for controlling a sterilization of at least one object by a fluid wherein the at least one object is positioned in a sterilization chamber of a sterilization apparatus, and wherein the object is exposed to the heated gaseous or liquid fluid, the method comprising the steps of:
    accelerating the fluid to a predetermined flow-speed by means of an acceleration device,
    transferring the fluid into a filter-chamber comprising a cone-formed inlet, wherein when passing through the cone-formed inlet, the fluid-flow laterally spreads from a cross section in the acceleration device to a larger cross section in the cone-formed inlet,
    separating particles from the fluid by a filter device,
    guiding the fluid through a plurality of openings of an orifice device arranged in the flow path of the fluid and
    determining the flow-speed of the fluid on the basis of a pressure difference across the orifice device wherein the pressure difference is derived and determined from a first pressure and from a second pressure, wherein the first pressure is measured in the fluid-flow upstream of the orifice device and downstream of the filter device and wherein the second pressure is measured in the fluid-flow downstream of the orifice device and upstream of the at least one object to be sterilized.

10. Method according to claim 9, characterized by determining the pressure difference by comparing a first fluid pressure measured upstream of the orifice device with a second fluid pressure measured downstream of the orifice device.

11. Method according to claim 10, wherein the flow-speed $\omega$ is calculated as $$\omega = \Phi \cdot \sqrt{\frac{2 \cdot \Delta p \cdot R_i \cdot (\tau + 273)}{p_{air}}},$$

with $R_i$ being a gas constant of air, $\Delta p$ being the determined pressure difference, $\tau$ being a measured fluid-temperature, $p_{air}$ being an ambient air pressure, and $\Phi$ being a characteristic value of the orifice device.

12. Method according to claim 9, further comprising
    comparing a measured value of the fluid-flow-speed with a predetermined minimum value of the fluid-flow-speed and/or with a predetermined maximum value of the fluid-flow-speed, and
    generating a flow-speed failure-signal when the measured value of the fluid-flow-speed exceeds the predetermined maximum value of the fluid-flow-speed or when the measured value drops below the predetermined minimum value of the fluid-flow-speed, and/or
    comparing a measured value of a fluid-temperature with a predetermined minimum value of the fluid-temperature and/or with a predetermined maximum value of the fluid-temperature, and
    generating a fluid-temperature failure-signal when the measured value of the fluid-temperature exceeds the predetermined maximum value of the fluid-temperature or when the measured value drops below the predetermined minimum value of the fluid-temperature.

13. Method of claim 12, wherein the predetermined minimum value of the fluid-flow-speed is 0.5 m/s and/or the predetermined maximum value of the fluid-flow-speed is 1.2 m/s.

14. Method of claim 12, wherein the predetermined minimum value of the fluid-temperature is around 200° C. and/or the predetermined maximum value of the fluid-temperature is around 500° C.

15. Method of claim 9, further comprising calculating the fluid-flow speed value on the basis of the determined pressure difference and a measured temperature of the fluid.

16. Method of claim 15, further comprising
determining whether the fluid is apt for a sufficient sterilization of the object on the basis of:
the determined flow-speed of the fluid,
a predetermined time period the at least one object rests in the sterilization chamber, and
the temperature of the fluid, and
generating a first signal for increasing and/or decreasing the fluid-flow-speed and/or generating a second signal for increasing and/or decreasing the fluid-temperature in response a determination that the fluid is not apt to sufficiently sterilize the at least one object.

17. Method of claim 12, further comprising processing a flow-speed failure signal and/or a fluid-temperature failure signal for stopping and/or throttling the acceleration device and/or the heating device.

\* \* \* \* \*